United States Patent
Mitchell et al.

(10) Patent No.: US 9,878,109 B2
(45) Date of Patent: Jan. 30, 2018

(54) MEDICAL DEVICE COMPRISING ILLUMINATION ARRANGEMENT

(75) Inventors: Andrew David Mitchell, Warwickshire (GB); Paul Richard Draper, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 777 days.

(21) Appl. No.: 14/130,457

(22) PCT Filed: Jun. 27, 2012

(86) PCT No.: PCT/EP2012/062399
§ 371 (c)(1),
(2), (4) Date: Dec. 31, 2013

(87) PCT Pub. No.: WO2013/004555
PCT Pub. Date: Jan. 10, 2013

(65) Prior Publication Data
US 2014/0155711 A1   Jun. 5, 2014

Related U.S. Application Data

(60) Provisional application No. 61/570,307, filed on Dec. 14, 2011.

(30) Foreign Application Priority Data

Jul. 1, 2011   (EP) .................................... 11172417

(51) Int. Cl.
*A61B 5/00* (2006.01)
*A61M 5/42* (2006.01)
(Continued)

(52) U.S. Cl.
CPC ............... *A61M 5/42* (2013.01); *A61B 5/145* (2013.01); *A61B 90/30* (2016.02); *A61M 5/00* (2013.01);
(Continued)

(58) Field of Classification Search
CPC . A61B 5/151; A61B 5/15103; A61B 5/15105; A61B 5/15126; A61B 5/153;
(Continued)

(56) References Cited

U.S. PATENT DOCUMENTS 5,720,761 A * 2/1998 Kaali ................. A61B 1/00087
                                                        600/101
6,011,889 A * 1/2000 Daniel .................. A61B 18/24
                                                        385/115
(Continued)

FOREIGN PATENT DOCUMENTS

CN          201631896 U    11/2010
DE           3322923 A1     1/1985
(Continued)

OTHER PUBLICATIONS

EP 11172417.5 Communication, European Search Report dated Aug. 10, 2011.

*Primary Examiner* — Max Hindenburg
(74) *Attorney, Agent, or Firm* — McDonnell Boehnen Hulbert & Berghoff LLP (57) ABSTRACT

The present invention relates to a medical device for intradermal or subcutaneous treatment of a patient, comprising: a piercing element to penetrate a skin portion of the patient; an illumination arrangement to illuminate the piercing element and/or to illuminate the skin portion prior and/or during a treatment process, wherein the illumination arrangement is further adapted to visually indicate a predefined treatment sequence of the treatment process.

15 Claims, 3 Drawing Sheets

(51) Int. Cl.
   *A61B 5/145*   (2006.01)
   *A61M 5/00*    (2006.01)
   *A61B 90/30*   (2016.01)

(52) U.S. Cl.
   CPC ....... *A61M 5/427* (2013.01); *A61M 2205/583* (2013.01)

(58) Field of Classification Search
   CPC ..... A61B 5/157; A61B 5/145; A61B 19/5202; A61B 90/30; A61M 5/00; A61M 5/427; A61M 2205/583
   See application file for complete search history.

(56) References Cited

U.S. PATENT DOCUMENTS

| | | | | |
|---|---|---|---|---|
| 6,584,335 | B1 * | 6/2003 | Haar | A61B 5/14532 |
| | | | | 600/322 |
| 7,964,412 | B2 * | 6/2011 | Brenneman | A61B 5/14532 |
| | | | | 422/500 |
| 7,981,049 | B2 | 7/2011 | Ritchie et al. | |
| 8,454,586 | B2 * | 6/2013 | Anastasie | A61B 18/24 |
| | | | | 606/15 |
| 8,465,977 | B2 * | 6/2013 | Joseph | G01N 33/48785 |
| | | | | 422/404 |
| 8,666,479 | B2 * | 3/2014 | Berndt | A61B 5/0075 |
| | | | | 600/476 |
| 9,358,369 | B1 * | 6/2016 | Webler, Jr. | A61B 1/00163 |
| 2005/0235993 | A1 | 10/2005 | Baecke et al. | |
| 2006/0124862 | A1 | 6/2006 | Rodriquez | |
| 2009/0076458 | A1 | 3/2009 | Nielsen et al. | |
| 2009/0227855 | A1 | 9/2009 | Hill et al. | |
| 2009/0247956 | A1 | 10/2009 | Devega | |

FOREIGN PATENT DOCUMENTS

| | | |
|---|---|---|
| DE | 102006018143 A1 | 10/2007 |
| EP | 2206529 A1 | 7/2010 |
| JP | 2006-284481 A | 10/2006 |
| JP | 2006-172362 A | 8/2009 |
| RU | 2012358 C1 | 5/1994 |
| RU | 2053744 C1 | 2/1996 |
| SU | 1745673 A1 | 4/1989 |
| WO | 0141837 A1 | 6/2001 |

* cited by examiner

MEDICAL DEVICE COMPRISING ILLUMINATION ARRANGEMENT

CROSS REFERENCE TO RELATED APPLICATIONS

The present application is a U.S. National Phase Application pursuant to 35 .S.C. § 371 of International Application No. PCT/EP2012/062399 filed Jun. 27, 2012, which claims priority to European Patent Application No. 11172417.5 filed Jul. 1, 2011 and U.S. Patent Provisional Patent Application No. 61/570,307 filed Dec. 14, 2011. The entire disclosure contents of these applications are herewith incorporated by reference into the present application.

FIELD OF INVENTION

The present invention relates to the field of medical devices and in particular to drug delivery devices or lancing devices having a piercing element to penetrate the skin of a patient.

BACKGROUND

User operated drug delivery devices are as such known in the art. They are typically applicable in circumstances, in which persons without formal medical training, i.e., patients, need to administer an accurate and predefined dose of a medicament, such as heparin or insulin. In particular, such devices have application, where a medicament is administered on a regular or irregular basis over a short-term or long-term period.

In order to accommodate these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose.

With patients suffering diabetes for instance, a blood glucose level has to be monitored and according to an actual measurement of said level an appropriate dose of insulin has to be administered on a regular basis. Blood glucose measurements as well as injection of a required dose of the medicament are quite often conducted by the patients themselves in different circumstances and situations. However, in rather dim or even dark environments, the process of piercing the skin may become rather difficult. Hence, a required degree of brightness or visibility for a lancing and/or for an injection process is not always available.

Document WO 01/41837 A1 discloses an injection device having a housing with a bow which can be pressed against and extend a skin surface where an injection is to be made. The bow is preferably made of a light transmitting material and can be illuminated by a lamp.

Moreover, document DE 33 22 923 A1 discloses an injection syringe with an illumination arrangement. There, the illumination arrangement is integrated into the syringe and is arranged lateral to the syringe for directing a focused light beam towards the distal tip of the injection needle. In this way, the site of needle puncture can be illuminated.

Even though various illumination arrangement already exist for syringe applications and injection devices, control and operation of the illumination requires a separate and additional interaction with the user or patient. In particular, the illumination has to be switched on and/or off separately. Also, the operation of an illumination arrangement is rather uncorrelated to the main functions of the injection device.

It is therefore an object of the present invention to provide a medical device having an improved illumination arrangement for illuminating a site of needle puncture in a comfortable and user-friendly way. The illumination arrangement should be easy and intuitively to control. The illumination arrangement should further improve user comfort and patient safety.

SUMMARY

The invention generally refers to a medical device for intradermal or subcutaneous treatment of a patient. For this purpose, the medical device comprises a piercing element to penetrate a skin portion of the patient. The device further comprises an illumination arrangement to illuminate the piercing element and/or to illuminate the skin portion, hence the site of needle puncture, at least during a treatment process. The illumination arrangement, in particular its control, is further adapted to visually indicate a predefined treatment sequence of the treatment process to be executed by or with the help of the medical device. The illumination arrangement, in particular its control, is adapted to coordinate illumination with the steps in a treatment process and/or with the status of the medical device.

With this particular feature, the illumination arrangement is not only adapted to illuminate a site of needle puncture and/or to illuminate the device itself but also to provide treatment-related information, for example timing information, to the user or patient prior, during or after a respective treatment process to be conducted and executed by way of the medical device.

In particular, the illumination arrangement is adapted to indicate the beginning, the end or various distinct intermediate steps of the treatment process. The illumination arrangement may be adapted to visualize, that the medical device is ready for use. Moreover, the illumination arrangement and its control may indicate a predefined time interval, the piercing element has to remain in or at the site of needle puncture. Also, the illumination arrangement may visually indicate a predefined dwell period, the piercing element should remain in biological tissue after delivery of the medicament in the tissue.

According to a preferred embodiment, the illumination arrangement is adapted to generate at least one light cone around the piercing element to illuminate the skin portion. Preferably, the illumination arrangement comprises a light source or at least a light-emitting aperture symmetrically arranged around the piercing element. It is of particular benefit, when the centre of the light cone substantially coincides with the piercing element. In this way, the site of puncture can be homogeneously illuminated, substantially irrespective of the orientation of the medical device.

According to another aspect, it is intended, that the illumination arrangement is adapted to generate various or variable light cones featuring a different cone angle, respectively. Moreover, the illumination arrangement may comprise different or multiple light sources, each of which being adapted to generate a light cone with a particular cone angle. Depending on the cone angle and the light intensity provided by the respective light source, either a rather bright and focused light spot may be incident on the skin portion and/or a rather large area of the skin may become subject to a rather faint or low level of illumination.

Moreover, it is even conceivable, that the illumination arrangement produces two different light cones simultaneously, wherein a rather focused inner light cone is entirely surrounded by an outer rather diverging and less intensive light cone. In this way, the outer light cone may provide a rather low level and ambient illumination wherein the inner light cone is particularly adapted and intended to brightly illuminate the site of skin puncture. By sufficiently illuminating the site of puncture, penetration angle and penetration depth can be easily controlled by the user or patient himself, even in a dim environment. The outer and ambient illumination cone may thus provide an illumination level sufficient for a rough orientation with respect to the site of puncture.

According to a further aspect, the illumination arrangement comprises at least one light source. The light source is preferably electrically driven. It may comprise an incandescent element, a gas discharge element, an electro-luminescent element or even laser-like optical elements providing stimulated emission radiation. In particular, the light source may comprise at least one light emitting diode (LED) providing a rather high luminous efficacy at a rather low degree of electrical power consumption. Preferably, the illumination arrangement also comprises at least one light reflecting and/or light deflecting element in order to provide a required beam shape and intensity distribution. The illumination arrangement may comprise at least one mirror or reflector and/or respective refractive and/or diffractive optical elements to modify and to shape the emitted light in a predefined way.

According to another aspect, the illumination arrangement is integrated into a housing of the device. Preferably, the illumination arrangement or its light emitting aperture is positioned near a distal end of the medical device pointing towards the skin portion during a treatment process. Preferably, the illumination arrangement or its light emitting aperture is arranged around the piercing element, e.g. near a distal end of a cartridge holder of e.g. a pen-type injector. In particular, when the piercing element is of disposable or replaceable type, the illumination arrangement and/or its light emitting aperture can be arranged near or even at an interface adapted to releasably connect the piercing element to the housing of the medical device.

According to a further preferred embodiment, the medical device comprises a control element adapted to at least partially correlate activation and/or deactivation of the illumination arrangement with the predefined sequence of the treatment process to be executed with the medical device. In particular, the control element is adapted to automatically activate and/or to deactivate the illumination arrangement depending on the user-controlled functionality of the medical device. If the medical device is for instance designed as a drug delivery device, such as a pen-type injector, setting of a dose of a medicament may be detected by the control element and may therefore automatically switch on the illumination arrangement. Additionally, also a dose injection action may trigger a different type or a supplemental illumination.

Moreover, the illumination arrangement is coupled with a control element adapted to control and/or to initiate the treatment process. For instance, the illumination arrangement, in particular its light source or its control element may be electrically connected with e.g. a dose dial or dose button of a drug delivery device. In this way, setting of a dose by activating or dialling a dose dial may inherently trigger to switch on the illumination arrangement. In the further process of treatment, depressing of a dose button to initiate dose injection or dose dispensing may be monitored accordingly and may be used to transfer the illumination arrangement into a different mode of operation. Hence, light intensity, cone angle or spectral composition of the emitted light may change appropriately. Moreover, also the end of a dose setting procedure prior to a dose dispensing action may be detected and may serve as a trigger to switch the illumination into a predefined illumination mode.

According to another preferred embodiment, the control element is even adapted to determine and/or to detect at least one distinct step of the treatment process. For instance, the control element may detect removal of a protective cap being indicative of the beginning of a treatment process. For instance, the control element may detect activation of an "arm" button, indicating that a dose has been set and that the injection process may start. Moreover, any manipulation of dose setting or dose dispensing elements of the medical device may be detected by the control element, which in response to such events may trigger a corresponding illumination, either of the device itself or of a skin portion to become subject to medical treatment.

Additionally, the control element may not only be adapted to switch on or to change the illumination. According to a further embodiment, the control element may be also adapted to modify and/or to deactivate the illumination provided by the illumination arrangement within a predefined temporal delay after reaching of or after determination of a distinct step of the treatment process. In particular with pen-type injectors it may be beneficial, when the end of an injection process is signalled by the illumination arrangement. Since an injection needle should stay in the skin tissue for a predefined dwell period after the dose of the medicament has been dispensed, the illumination arrangement may be used to indicate the duration of said dwell period, which is typically in the range of a few seconds.

Therefore and according to another preferred embodiment, the illumination arrangement is adapted to indicate a particular treatment sequence, e.g. a dwell period, by at least two different illumination colours and/or by way of different illumination schemes.

According to one approach, the duration of a predefined treatment sequence may be indicated by a flashing or blinking of the illumination arrangement. Furthermore, the illumination sequence may intuitively indicate the end of a particular treatment step, e.g. by a varying illumination sequence. Hence, the frequency of a blinking may increase or decrease until the light pattern emitted by the illumination arrangement either approaches a constant or zero intensity level. Apart from modifying the colour or the spectral composition of the emitted light, it is also conceivable, that the illumination arrangement is adapted to modify the intensity or attenuation of the light.

According to a further preferred aspect, the medical device comprises a drug delivery device, particularly adapted and designed for injecting a liquid medicament. The drug delivery device is preferably designed as a pen-type injector for conducting self-medication of various medicaments. In a further preferred aspect, the drug delivery device comprises a housing to accommodate a cartridge being at least partially filled with a medicament to be injected. The drug delivery device further comprises a drive mechanism having a piston rod to become operably engaged with a piston of the cartridge. The piston is slidably arranged in the cartridge and provides a proximal seal for the cartridge.

A distal end of the cartridge, typically sealed by a pierceable or penetrable septum is to be coupled with the piercing element typically comprising an injection needle. This way and by exerting distally directed thrust to the piston of the cartridge, a predefined dose of the medicament can be expelled through the injection needle and can thus be administered to biological tissue.

It may be of further benefit, when the cartridge is readily disposed and arranged in the housing of the medical device. The medical device, in particular the drug delivery device may be of disposable type. Hence, instead of replacing an empty cartridge, the entire device may be discarded when the content of the cartridge is used up. Alternatively, it is also conceivable, that the cartridge is replaceable. Hence, the housing of the drug delivery device can be disassembled and re-assembled in order to provide cartridge replacement.

In a further aspect, the medical device may comprise a lancing device adapted to pierce and/or to analyze biological fluid and/or biological tissue. In particular, the lancing device comprises a needle to puncture a blood vessel in order to extract and to measure a blood glucose level or other physiological substances or parameters.

In effect and according to another preferred aspect, actuation of the control element of the medical device may turn on and activate the illumination arrangement at least for a predefined time interval. The invention therefore provides fully or semi-automated activation, modification and/or deactivation of an illumination arrangement of a medical device to enhance patient safety and to guide the user through the treatment process to be conducted with the medical device.

Furthermore, and according to an independent aspect, the invention also relates to a method of controlling an illumination arrangement of a medical device. Here, in a first step, at least one treatment sequence of a predefined treatment process to be executed by the medical device is detected. In response to said detection, the control of the illumination arrangement may automatically modify, activate and/or deactivate the illumination arrangement, wherein further parameters, like a predefined delay or temporal offset may be additionally implemented to correlate to at least one particular treatment sequence of the treatment process with a modification, activation and/or deactivation of the illumination arrangement.

Alternatively or additionally, the method may provide visually indicating at least one predefined treatment sequence of the treatment process by means of the illumination arrangement. In this way, the patient and/or user of the device can be visually guided through and informed about the treatment process in general and the single treatment steps to be conducted sequentially.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in detail by making reference to the drawings in which.

DETAILED DESCRIPTION

Figure 1:
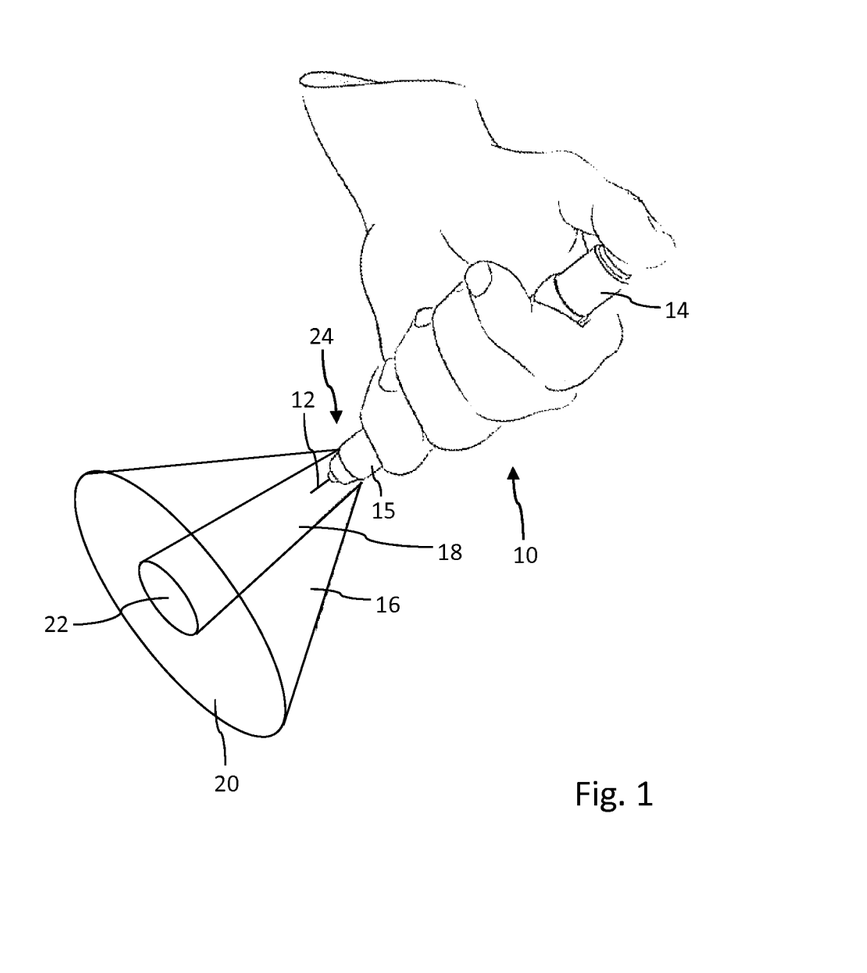
FIG. 1 schematically illustrates a medical device in form of a pen-type injector adapted to generate two different light cones during a dose dispensing action, FIG. 2 schematically shows a lancing device equipped with an illumination arrangement.

The sketch of FIG. 1 schematically illustrates a typical application scenario when using a pen-type injector 10 for injecting a dose of a medicament. The drug delivery device 10 comprises a dose button 14 at a proximal end which is to be depressed by a thumb of a user. The drug delivery device 10 comprises a cartridge holder 15 at a distal portion which is further equipped with a replaceable injection needle 12.

Typically, the injection needle 12 is provided on a needle hub to be screwed onto a distal interface of the cartridge holder 15. As further depicted in FIG. 1, the cartridge holder 15 is equipped with an illumination arrangement 24 which is adapted to generate two different cones of light 16, 18. Whereas the rather focused inner cone of light 18 is intended to illuminate a site of needle puncture 22 on the skin of the patient, the outer cone of light 16 concentrically arranged relative to the inner cone of light 18 is adapted to provide ambient illumination of the surrounding area 20 of the particular skin portion 22 to become subject to medical treatment.

Figure 3:
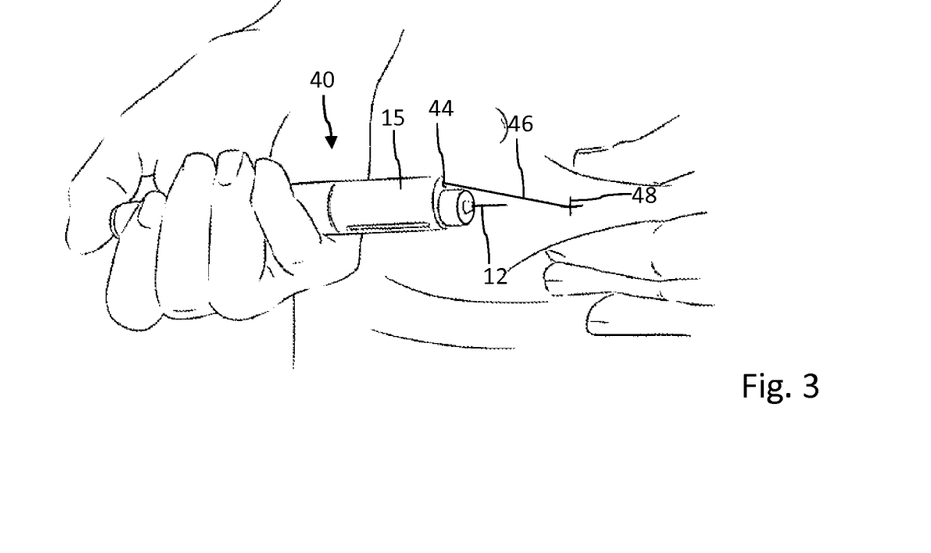
FIG. 3 shows another application scenario of a pen-type injector.

A rather similar device 40 is illustrated in FIG. 3 but there, instead of an illumination arrangement 24 concentrically enclosing the injection needle 12, a single light source 44 is provided at a distal end face of a cartridge holder 15. As shown in FIG. 3, the light source 44 is preferably designed as LED or as a laser adapted to emit a rather focused light beam 46 to a target area 48 on the skin of the patient. Here, the target area 48 marks the site of needle puncture.

Figure 2:
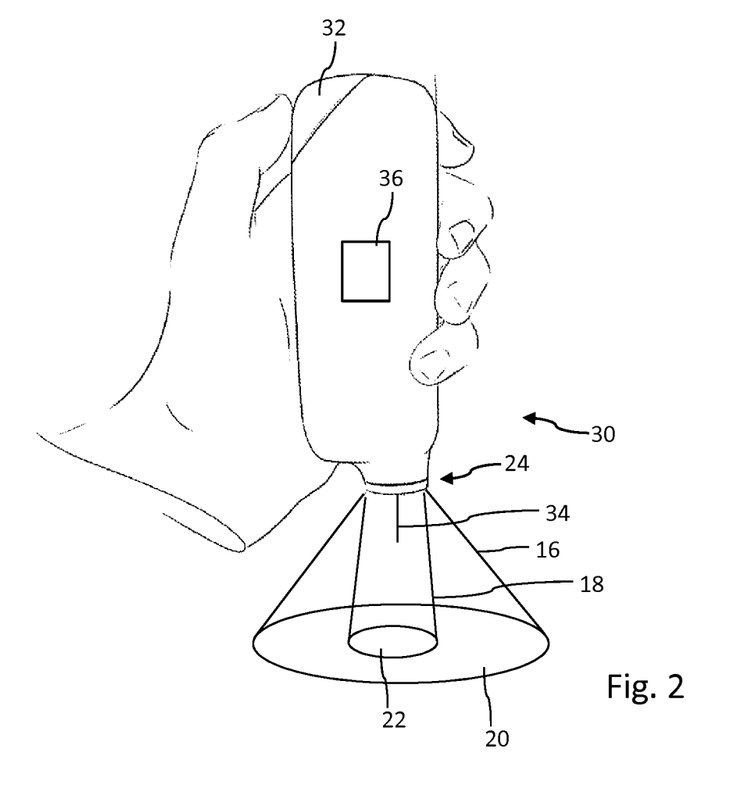

FIG. 2 is further illustrative of a lancing device 30 having a piercing needle 34 adapted to puncture or to pierce the skin tissue of the patient, e.g. for the purpose of a blood glucose measurement. The lancing device 30 is equipped with an illumination arrangement 24 similar to the one already described with respect to FIG. 1. The illumination arrangement 24 is adapted to generate two different cones of light 16, 18, which may be activated sequentially or simultaneously and may feature equal, similar or different spectral compositions and light intensities.

Furthermore, a control button 32 to be depressed by a thumb of a user's hand is illustrated. If, for instance, the control button 32 is depressed by the user, the entire device 30 will be switched on to support a medical treatment process. Depression of said button 32 may be detected by the control element 36, which, depending on a predefined schedule may activate or deactivate the cones of light 16, 18, either for a predefined time interval and/or until a stop signal is received by the control element 36.

Figure 4:
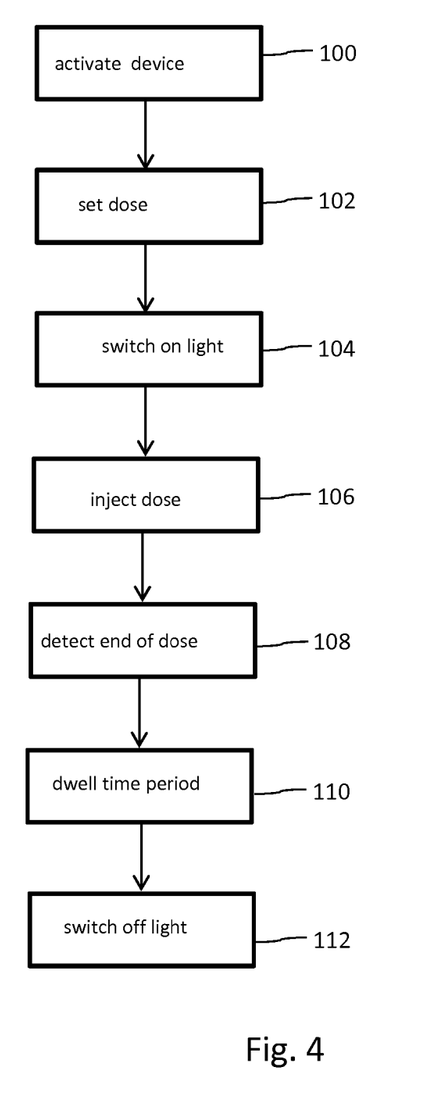
FIG. 4 is illustrative of a flowchart of a first operation mode of the medical device.

The flowchart according to FIG. 4 illustrates an example on how the illumination arrangement 24, 44 can be correlated with the overall handling of e.g. a drug delivery device 10, 40. In a first step 100, the device is activated. For instance a semi- or fully-automated device is switched on. Also, such activation 100 of the device 10, 30, 40 may be automatically sensed, e.g. by removing a protective cap. In a subsequent step 102, a dose to be injected by means of the drug delivery device 10, 40 is set, e.g. by actuation of a respective dose setting element 14 of the device 10. The dose setting, in particular the termination of a dose setting procedure may also be automatically detected by a control element 36, for example by detection of a button press of an "arm" button. In response to said detection, the illumination arrangement 24, 44 may be switched on in step 104.

Activation of the illumination arrangement 24, 44 may lead to a sequential or simultaneous generation of the cones of light 16, 18. In a subsequent step 106 the dose previously set is injected into the skin portion 22, 48 by making use of the illumination provided by the illumination arrangement 24, 44.

In a subsequent step 108, termination or end of the injection process is detected. With a semi-automated drug delivery device 10, 40, the end of an injection procedure can be detected by a substantial decrease of the thrust exerted by the thumb of a user. Hence, when the force level acting on a piston of a cartridge arranged inside a drug delivery device 10, 40 drops below a predefined threshold, a clear indication of the end of an injection process is generally given.

With respect to the illumination arrangement and its control, the end of an injection process may trigger a delay or a dwell period. Hence, in the following step 110, the illumination is kept on for a predefined period of time, which is in the range of a few seconds, e.g. around 5 to 10 seconds. Thereafter, in step 112, the illumination is automatically switched off, thereby indicating to the user the end of the dwell period.

In this way, the illumination arrangement 24 is indicative to the user that the predefined dwell period has elapsed and that the injection needle 12 can now be removed from the skin portion 22.

Figure 5:
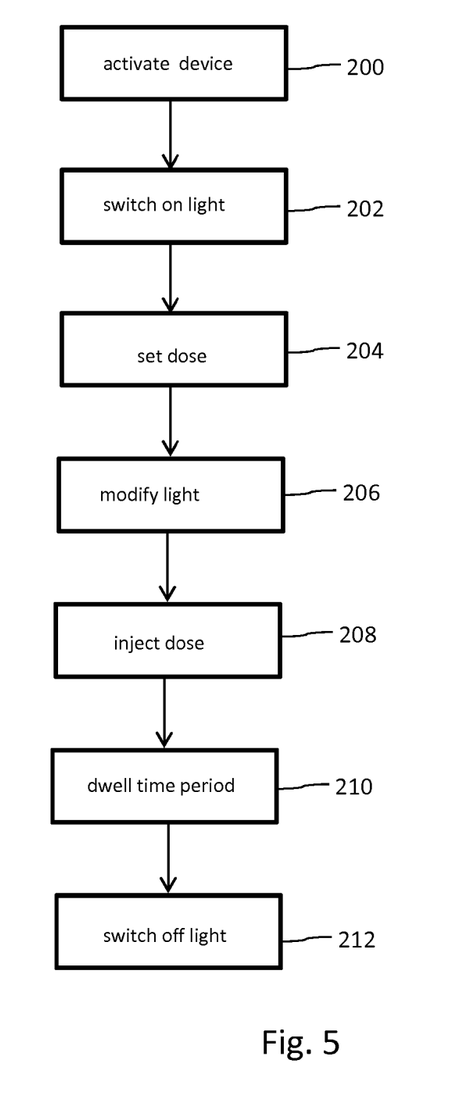
FIG. 5 shows a flowchart of another operation mode of the illumination arrangement.

FIG. 5 is further illustrative of an alternative way on how to operate the illumination arrangement. In a first step 200, the medical device is activated. But here, already prior to a setting of a dose in step 204, the illumination arrangement 24, 44 is switched on in the first step 202. Accordingly, the illumination arrangement 24, 44 may be particularly adapted to illuminate a scale or a comparable display of the medical device 10, 30, 40 in order to enable and/or to facilitate the procedure of dose setting, even in dark or dim environments. In the proceeding step 204, the dose to be dispensed by the device 10, 40 is set and at the end of the dose setting, prior to a dose injecting to be conducted as step 208, the illumination arrangement is switched into a different illumination mode in step 206.

The illumination mode to be activated in step 206 is particularly intended and adapted to accompany the injection process conducted in step 208. The illumination mode activated in steps 202 and 206 may differ with respect to spectral composition, spatial light distribution, light intensity and/or with respect to a sequence of on-off cycles.

During the injection process 208 the illumination is sustained. After completion of the actual injection process 208, the control of the illumination arrangement is adapted to provide a delay in step 210 during which the illumination is kept in an activated state before in a final step 212, e.g. after elapsing of a predefined dwell period, the illumination is finally switched off.

The described steps are only exemplary of two of a plurality of modes the device can be operated. In general, the device may comprise various sensors, e.g. to automatically detected various steps of the treatment process to be executed by the device. Hence, the device may be equipped with pressure and/or position sensor, in order to track and to monitor a dose setting and/or dispensing action conducted by the user. Depending on the signals to be generated by such sensors, the illumination can be modified, e.g switched on and/or off appropriately without any further user interaction.

The invention claimed is:

1. A medical device for intradermal or subcutaneous treatment of a patient, comprising:
    a piercing element to penetrate a skin portion of the patient;
    an illumination arrangement to illuminate the piercing element and/or to illuminate the skin portion at least during a treatment process,
    wherein the illumination arrangement is further adapted to visually indicate a predefined treatment sequence of the treatment process;
    wherein the illumination arrangement comprising a control element adapted to at least partially correlate activation of the illumination arrangement with the predefined sequence of the treatment process.

2. The medical device according to claim 1, wherein the illumination arrangement is adapted to generate at least one light cone around the piercing element to illuminate the skin portion.

3. The medical device according to claim 2, wherein the illumination arrangement is adapted to generate various light cones of different cone angle.

4. The medical device according to claim 1, wherein the illumination arrangement comprises at least one light source of incandescent, gas discharge, electro-luminescent or stimulated emission type.

5. The medical device according to claim 1, wherein the illumination arrangement is adapted to indicate the beginning, the end or various distinct intermediate steps of the treatment process.

6. The medical device according to claim 5, wherein the control element is adapted to determine and/or to detect at least one distinct step of the treatment process.

7. The medical device according to claim 6, wherein the control element is adapted to modify and/or to deactivate the illumination of the illumination arrangement within a predefined delay after reaching of or determination of the distinct step of the treatment process.

8. The medical device according to claim 1, wherein the illumination arrangement is adapted to indicate the treatment sequence by at least two different illumination colours and/or by way of different illumination sequences.

9. The medical device according to claim 1, comprising a drug delivery device for injecting a liquid medicament.

10. The medical device according to claim 9, wherein the drug delivery device comprises:
    a housing to accommodate a cartridge at least partially filled with a medicament to be injected,
    a drive mechanism comprising a piston rod to become operably engaged with a piston of the cartridge.

11. The medical device according to claim 9, further comprising a cartridge disposed in the housing.

12. The medical device according to claim 1, comprising a lancing device to pierce and/or to analyze biological fluid and/or biological tissue.

13. The medical device according to claim 1, wherein the illumination arrangement is coupled with a control element adapted to control and/or to initiate the treatment process.

14. The medical device according to claim 13, wherein actuation of the control element turns on the illumination arrangement for a predefined time interval.

15. A method of controlling an illumination arrangement of a medical device according to claim 1, comprising the steps of:
    detecting at least one treatment sequence of a predefined treatment process to be executed by the medical device,
    modifying the operation mode of an illumination arrangement of the medical device in response to the detection of the treatment processes, and
    visually indicating at least one predefined treatment sequence of the treatment process by means of the illumination arrangement.

* * * * *